(12) United States Patent
Chan

(10) Patent No.: US 7,682,325 B2
(45) Date of Patent: Mar. 23, 2010

(54) ADJUSTABLE DORSAL SPLINT

(76) Inventor: Shu-Chen Chan, No.260-5, Lane 58, Nanyang Rd., Fongyuan City, Taichung County (TW)

( * ) Notice: Subject to any disclaimer, the term of this patent is extended or adjusted under 35 U.S.C. 154(b) by 15 days.

(21) Appl. No.: 12/133,941

(22) Filed: Jun. 5, 2008

(65) Prior Publication Data
US 2009/0306566 A1 Dec. 10, 2009

(51) Int. Cl.
*A61F 5/00* (2006.01)
(52) U.S. Cl. ........................................ 602/23; 128/882
(58) Field of Classification Search .................. 602/23, 602/27, 28–29; 128/882; 2/22, 24, 455
See application file for complete search history.

(56) References Cited

U.S. PATENT DOCUMENTS

| | | | | |
|---|---|---|---|---|
| 5,031,240 A | * | 7/1991 | Nierhaus | .......................... 2/24 |
| 5,776,090 A | * | 7/1998 | Bergmann et al. | ............ 602/28 |
| 5,898,939 A | * | 5/1999 | Schramm | .......................... 2/22 |
| 6,145,134 A | * | 11/2000 | Davis et al. | .................... 2/463 |
| 2005/0076421 A1 | * | 4/2005 | Littzi | ............................ 2/239 |

FOREIGN PATENT DOCUMENTS

WO    WO 03063622 A2 * 8/2003

\* cited by examiner

*Primary Examiner*—Michael A. Brown
(74) *Attorney, Agent, or Firm*—Egbert Law Offices PLLC

(57) ABSTRACT

The present invention provides an adjustable dorsal splint for resolving the shortcomings of a typical fixation splint. The invention includes a fixation splint, which contains a splint body, a first retaining portion, and a second retaining portion. A curvature adjustment portion is placed at a preset location of the splint body of the fixation splint, so as to adjust the splint body into predefined bending angle. As the fixation splint is provided with a curvature adjustment portion, it is possible to flexibly adjust the bending angle of the fixation splint to mate with the foot of the patient, thereby maintaining the position of the feet with better efficiency.

3 Claims, 5 Drawing Sheets

ADJUSTABLE DORSAL SPLINT

CROSS-REFERENCE TO RELATED U.S. APPLICATIONS

Not Applicable.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable.

REFERENCE TO AN APPENDIX SUBMITTED ON COMPACT DISC

Not Applicable.

BACKGROUND OF THE INVENTION

1. Field of the Invention

The present invention relates generally to a fixation splint, and more particularly to an innovative splint with an adjustable structure for medical treatment and health care.

2. Description of Related Art Including Information Disclosed Under 37 CFR 1.97 and 37 CFR 1.98

As for drop foot, Achilles tendonitis, heel pain, plantar fasciitis or lower extremity overuse injuries patients, there are similar rehabilitation products available in the market for patients suffering from the foregoing conditions. At present, current rehabilitation products are based on general size of a universal foot. One method of one injection mold is made for a splint.

As each patient has a foot with a particular bone size, the current single size splint cannot meet the needs of injured patients for necessary adjustments. Therefore, the prior art splint is not completely suitable for each individual patient.

Furthermore, during nighttime application, the injured patients will turn the body over unconsciously, exposing risk and creating vulnerability to oppression or arching, causing secondary injury when sleeping. The secondary injury causes delay of rehabilitation.

To this end, a fixation splint 10 is developed for the benefit of patients during sleeping. As shown in FIG. 1, a predefined bending plate is shown, where a first and second retaining device 11, 12 is separately defined on the front and rear part for fixing the foot bones and sole. A long groove 13 for threading a bandage is preset onto the first and second retaining device 11, 12, so that the bandage could be used to fix securely the fixation splint 10 onto the injury point. However, shortcomings are observed during actual applications.

The fixation splint 10 is often fabricated by means of ejection molding, and the plate is bent to a fixed angle. When the fixation splint 10 is retained on the feet of the patient, the feet are forcibly adapted to the bent angle. Owing to different forms and bending angle of the feet, the fixation splint 10 cannot be adjusted flexibly to meet the demands of individual patients, possibly leading to greater damage and extended recovery time.

Furthermore, the typical fixation splint 10 is made of plastic materials of a certain thickness. So, brittle rupture for such fixation splint 10 may likely occur, leading to excessive waste of materials.

Thus, to overcome the aforementioned problems of the prior art, it would be an advancement in the art to provide an improved structure that can significantly improve efficacy.

Therefore, the inventor has provided the present invention of practicability after deliberate design and evaluation based on years of experience in the production, development and design of related products.

BRIEF SUMMARY OF THE INVENTION

There is enhanced efficacy of the present invention over the prior art. In the prior art, the bending angle of the typical fixation splint is fixed during molding and fabrication. Thus, it is impossible to adjust the curvature according to different forms of foot bones, thus leading to mismatching and inconvenience issues. Also, as the typical fixation splint 10 is made of plastic materials of a certain thickness, brittle rupture for such fixation splint 10 may likely occur, leading to excessive waste of materials without possible recycling.

Based on the present invention, the splint body of fixation splint is provided with a curvature adjustment portion. The patient is allowed to adjust the bending curvature of the fixation splint for matching the foot bones. Moreover, the adjusting bandages are tied for fixation purposes, namely, the hurt foot is fastened by the fixation splint, thus avoiding possible reoccurrence of damage and accelerating the recovery process.

As the fixation splint of the present invention is made of a metal material with better rigidity and strength, it is possible to fabricate a thin-profile fixation splint and to recycle the fixation splint once the patient is recovered physically, thus preventing any excessive waste of materials with improved applicability.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
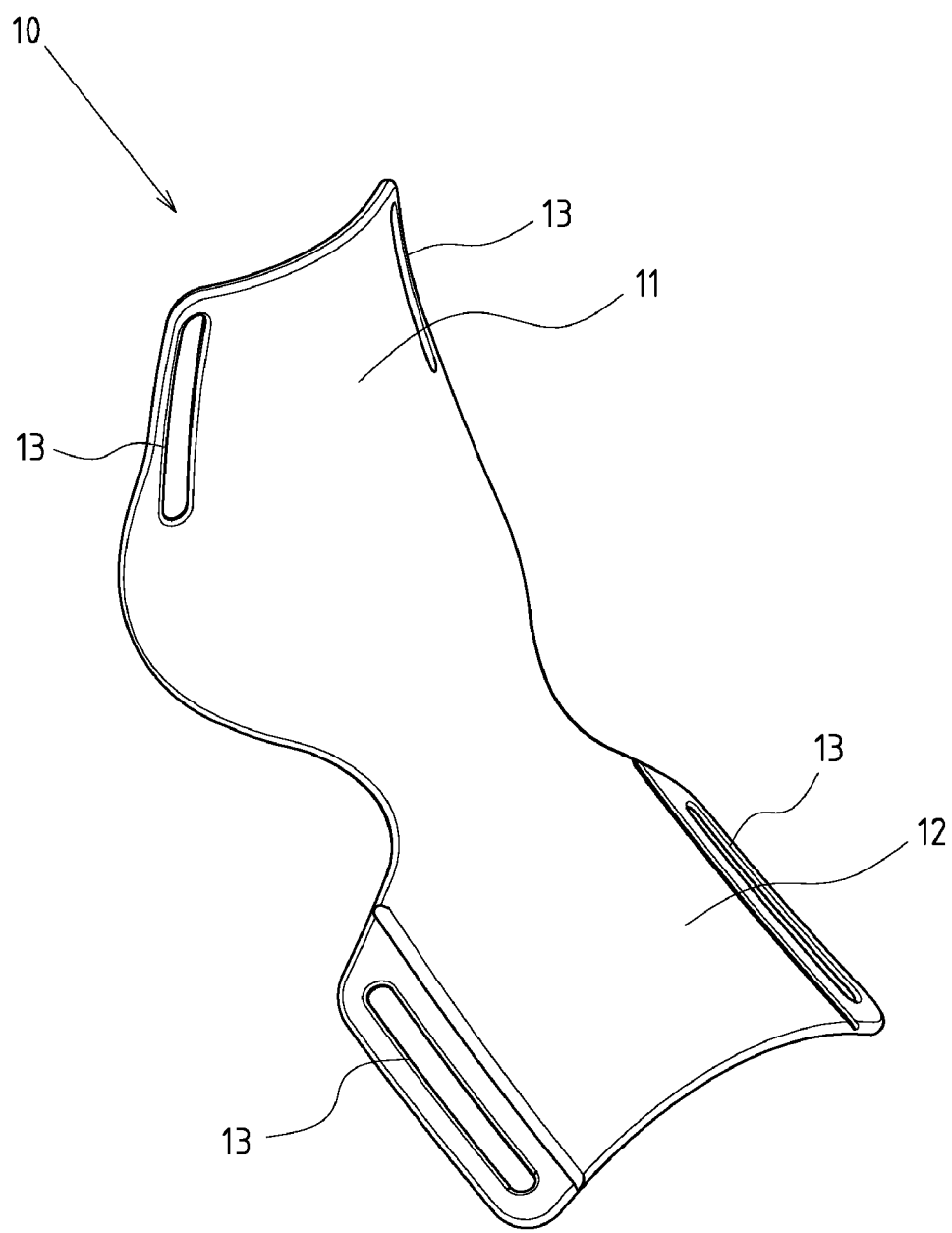
FIG. 1 depicts a perspective view of the conventional model.

The features and the advantages of the present invention will be more readily understood upon a thoughtful deliberation of the following detailed description of a preferred embodiment of the present invention with reference to the accompanying drawings.

FIGS. 2-5 depict preferred embodiments of adjustable dorsal splint of the present invention. The embodiments are provided only for explanatory purposes with respect to the patent claims.

The adjustable dorsal splint ties onto the feet for fixation purposes. The splint comprises: a fixation splint 20, containing a splint body 21, a first retaining portion 22 and second retaining portion 23 extended from both ends of the splint body 21. A curvature adjustment portion 24 is placed at a preset location of the splint body 21 at the fixation splint 20, so as to adjust the splint body 21 into a flexible bending angle. The curvature adjustment portion 24 may be bent into a flexible section. The fixation splint 20 is made of metal material.

The fixation splint 20 could be assembled into a jacket 30. One end of which is provided with an opening 31 to define a holding space 32 in the jacket 30, so as to accommodate the fixation splint 20. At least two adjusting bandages 33, 34 are circumferentially arranged onto the jacket 30, such that the jacket 30 sleeved with the fixation splint 20 could be tied onto the feet. Adhesive portions 330, 340 are placed at both ends of the adjusting bandages 33, 34, so two adjusting bandages 33, 34 can be adhered onto preset location of the jacket 30.

Figure 2:
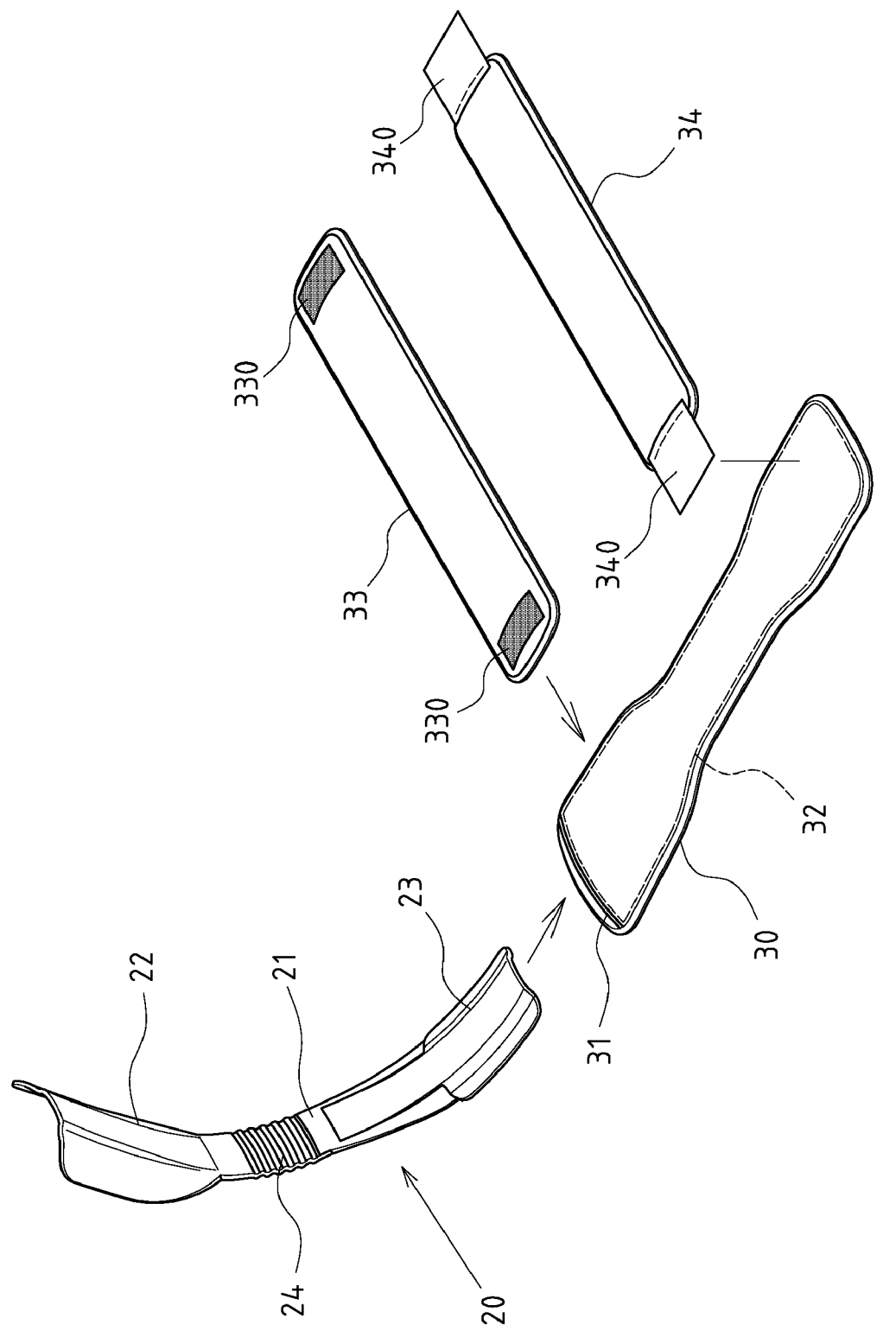
FIG. 2 depicts an exploded perspective view of the present invention.
Figure 3:
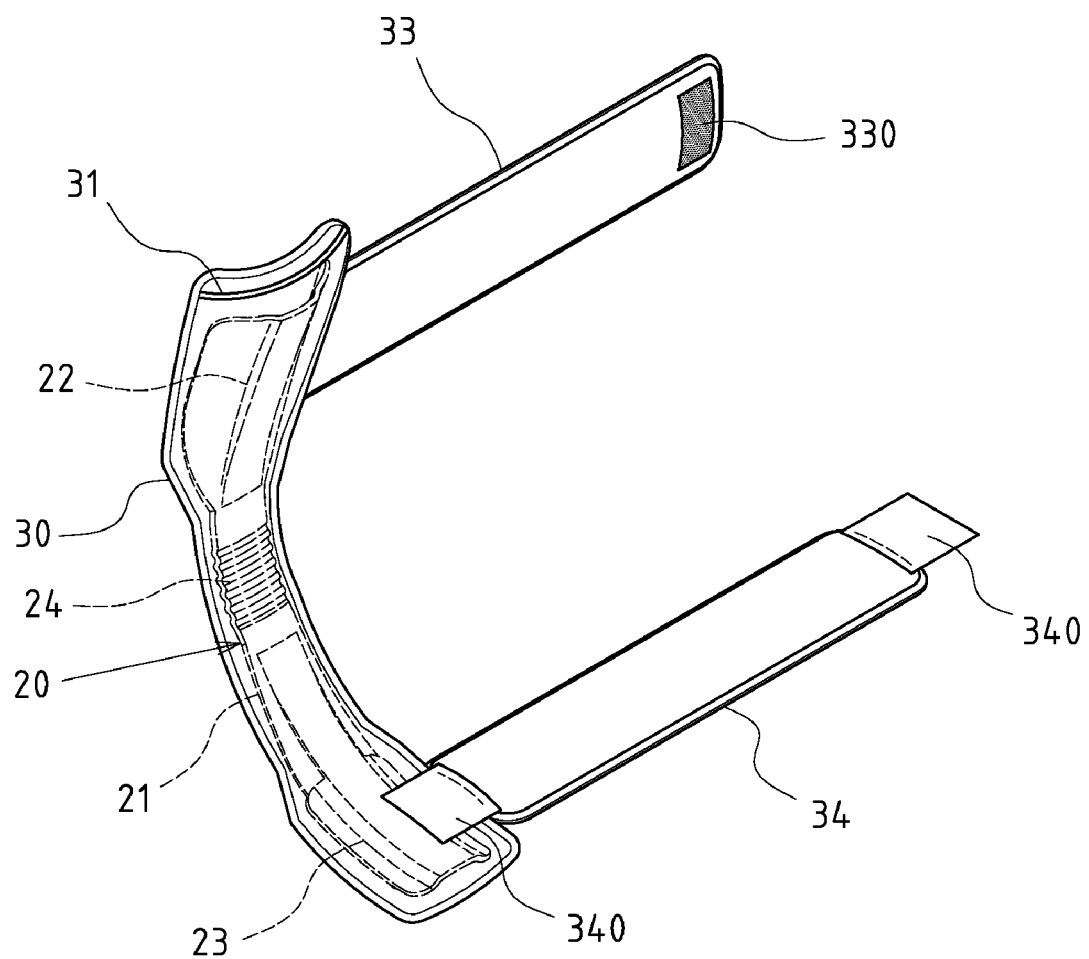
FIG. 3 depicts an assembled perspective view of the present invention.
Figure 4:
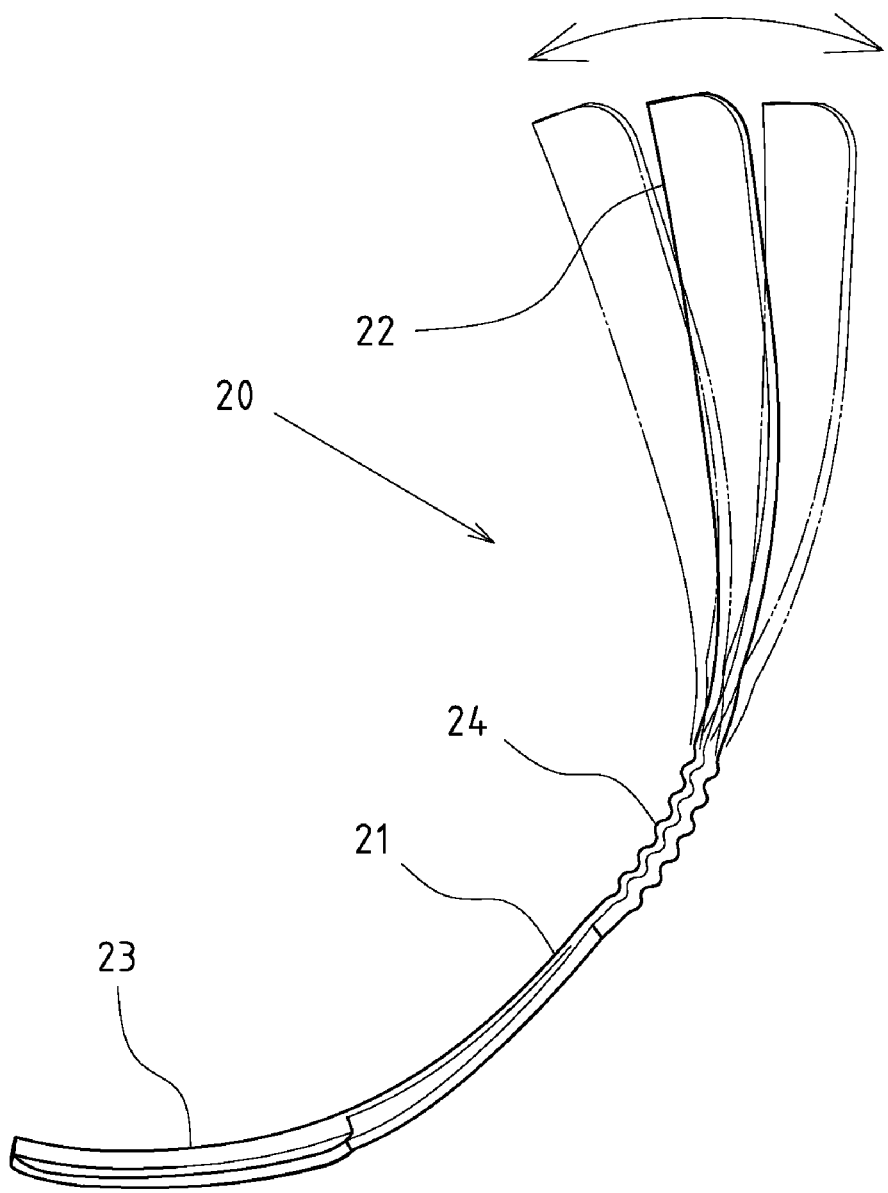
FIG. 4 depicts a side elevation view of the operation of the curvature adjustment portion of fixation splint of the present invention.
Figure 5:
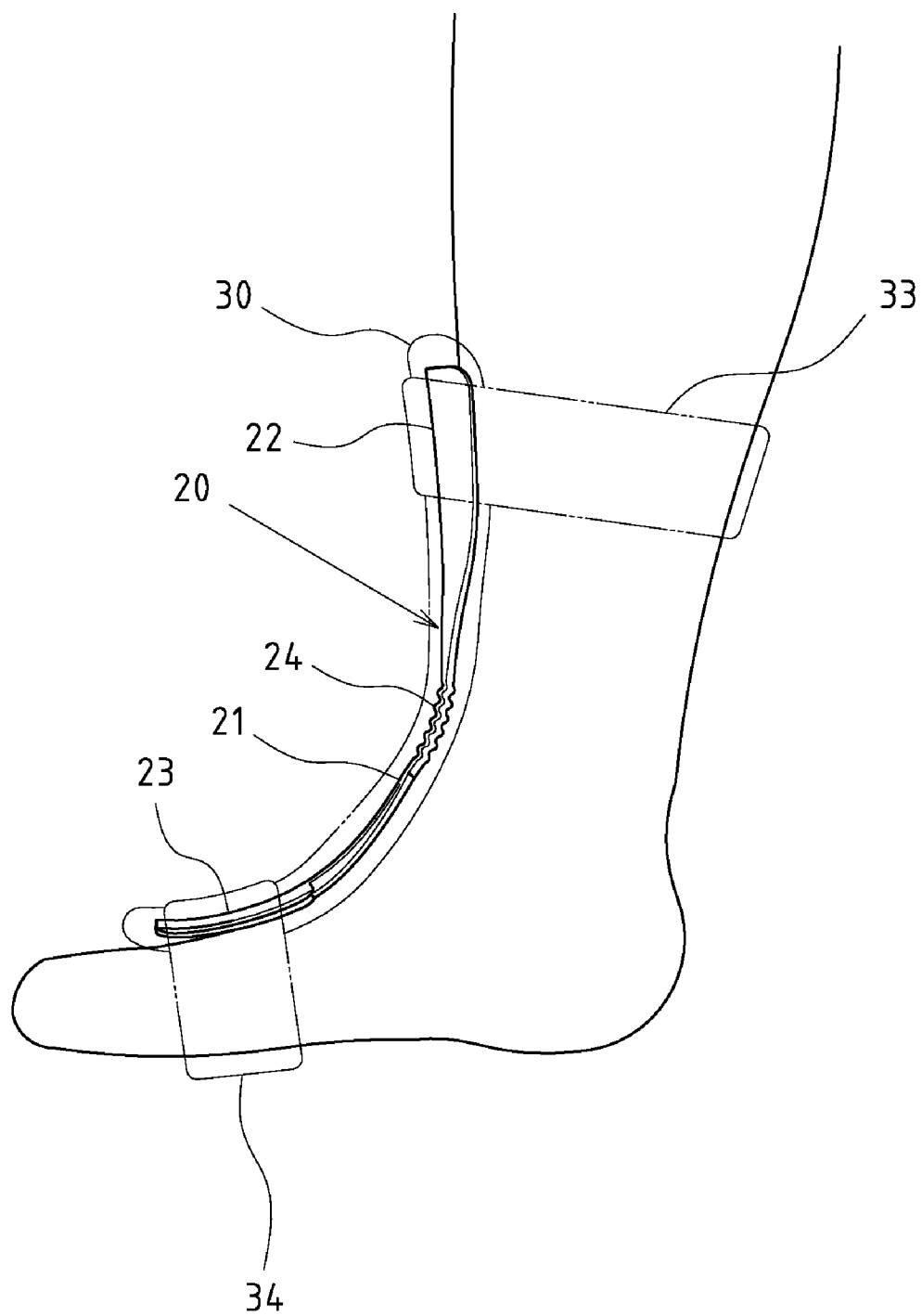
FIG. 5 depicts a schematic view of the operation of the present invention.

Based on above-specified structures, the present invention is operated as follows:

Referring to FIGS. 2, 3, and 5, the patient may, prior to sleeping, sleeve the fixation splint 20 into the opening 31 of the jacket 30, and adhere two adjusting bandages 33, 34 separately onto both ends of the jacket 30, i.e. at the first retaining portion 22 and second retaining portion 23 of the fixation splint 20, and then place the jacket 30 between the ankle and feet skeleton. In this way, the first retaining portion 22 could be retained onto the foot back, and the second retaining portion 23 could be retained onto the foot skeleton, as shown in FIG. 4. Since the splint body 21 of the fixation splint 20 is provided with a curvature adjustment portion 24, the patient is allowed to adjust the fixation splint 20 depending on its own form of the foot bones by manually holding the first and second retaining portions 22, 23 of the fixation splint 20, and applying slight inward or outward force to change the bending curvature of the curvature adjustment portion 24 in tune with the bones of the patient. Next, the adjusting bandages 33, 34 at both ends of the jacket 30 could be separately tied onto the foot skeleton and sole. Adhesive portions 330, 340 at one end of the adjusting bandages 33, 34 are adhered onto the adjusting bandage 33, 34 for fixation purposes. During sleeping, the hurt foot could be fastened by the adjustable fixation splint 20, thus avoiding possible reoccurrence of damage.

As the jacket 30 is made of heat-retaining materials, the patient will not feel cold in chilly weather.

I claim:

1. An adjustable dorsal splint apparatus comprising:
 a fixation splint having a splint body with a first retaining portion and a second retaining portion integral therewith, said first retaining portion extending from one end of said splint body and a second retaining portion extending from an opposite end of said splint body, said splint body having a corrugated adjustment portion formed thereon so as to allow said splint body to be bent to a desired angle;
 a jacket having an opening at one end thereof such that said fixation splint is entirely received therethrough into a holding space within said jacket; and
 a pair of adjustment bandages separate of said jacket and extendable around said jacket so as to allow said fixation splint to be fixed to a foot and lower leg of a user.

2. The adjustable dorsal splint apparatus of claim 1, said pair of adjustment bandages each having an adhesive portion positioned at opposite ends thereof so as to allow the adjustment bandage to be adhered to a preset location on said jacket.

3. The adjustable dorsal splint apparatus of claim 1, said fixation splint being formed of a metal material.

* * * * *